United States Patent [19]

Nielsen et al.

[11] 4,267,073

[45] May 12, 1981

[54] ETHYLENE OXIDE CATALYST

[75] Inventors: Robert P. Nielsen; Albert A. Jecminek, both of Houston, Tex.

[73] Assignee: Shell Oil Company, Houston, Tex.

[21] Appl. No.: 104,229

[22] Filed: Dec. 17, 1979

Related U.S. Application Data

[63] Continuation of Ser. No. 916,437, Jun. 19, 1978, abandoned, and a continuation-in-part of Ser. No. 816,569, Jul. 18, 1977, abandoned, which is a continuation of Ser. No. 652,603, Jan. 26, 1976, abandoned.

[51] Int. Cl.$^3$ .......................... B01J 23/08; B01J 23/66
[52] U.S. Cl. ............................... 252/455 R; 252/454; 252/463; 252/476; 260/348.34
[58] Field of Search ................... 252/454, 455 R, 463, 252/476; 260/348.34

[56] References Cited

U.S. PATENT DOCUMENTS

| | | | |
|---|---|---|---|
| 2,366,724 | 1/1945 | Gardner | 260/348.32 |
| 3,125,538 | 3/1964 | Arnold, Jr. et al. | 252/454 |
| 3,144,416 | 8/1964 | Hosoda et al. | 252/476 |
| 3,575,888 | 4/1971 | Long | 252/476 |
| 3,702,259 | 11/1972 | Nielsen | 252/463 X |
| 3,962,136 | 6/1976 | Nielsen et al. | 252/454 |
| 4,039,561 | 8/1977 | Mitsuhata et al. | 260/348.34 |
| 4,169,099 | 9/1979 | Khoobiar | 260/348.34 |

Primary Examiner—Carl F. Dees

[57] ABSTRACT

Catalysts with improved selectivities for the production of ethylene oxide are prepared by the addition of selected amounts of thallium to silver based supported catalysts.

28 Claims, No Drawings

ETHYLENE OXIDE CATALYST

This is a continuation of application Ser. No. 916,437, filed June 19, 1978, and now abandoned, and a continuation-in-part of application Ser. No. 816,569 filed July 18, 1977, now abandoned, which is a continuation of application Ser. No. 652,603, filed Jan. 26, 1976, now abandoned.

BACKGROUND OF THE INVENTION

1. Field of the Invention

This invention is related to improved silver catalysts for the production of ethylene oxide, their preparation, and their use in ethylene oxide processes.

2. The Prior Art

Materials consisting of silver upon a support are known to be useful catalysts for the production of ethylene oxide by the controlled incomplete oxidation of ethylene with molecular oxygen. A great variety of modifications have been proposed to improve the activity and selectivity of these catalysts. These modifications have involved, for example, the supports employed, the method of production, the physical form of the silver on the support and the addition of additives to the catalyst.

The alkali and alkaline earth metals and their salts have been repeatedly proposed as additives for various silver ethylene oxide catalysts. Carter, in U.S. Pat. No. 2,125,333, issued Aug. 2, 1938, was among the first to disclose alkali metal addition. He specified the use of "small amounts" of alkali metals, including both sodium or potassium in his silver catalyst. Later patents elaborated on this disclosure. McNamee et al in U.S. Pat No. 2,238,474, issued Apr. 15, 1941, disclosed that while addition of 100 ppm by weight to 24% by weight of sodium improved silver catalysts, these amounts of potassium had a detrimental effect on catalyst performance. Sears, Jr. et al in U.S. Pat. No. 2,615,900, issued Oct. 28, 1952, cited a large number of promoters useful in broad weight ranges. Saken, in U.S. Pat. No. 2,671,764, issued Mar. 9, 1954 disclosed the use of large amounts of alkali metal sulfates. Hosoda et al in U.S. Pat. No. 3,144,416, issued Aug. 11, 1964, also cited a number of promoter materials. Kriger et al in U.S. Pat. No. 3,563,913 issued Feb. 16, 1971, generally disclosed the use of alkali and alkaline earth metals as promoters.

Cusumano in U.S. Pat. No. 3,844,981 disclosed the use of promoters selected form Groups VII-B, I-B or the iron group of Group VIII of the percdic table of the elements. Belgian Pat. No. 822,857 issued June 6, 1975, also disclosed a large number of promoters in addition to alkali and alkaline earth promoters. Belgium Pat. No. 819,654, issued Dec. 31, 1974, disclosed the use of thallium in conjunction with another metal or metals. Gardner, U.S. Pat. No. 2,366,724, issued Jan. 9, 1945 teaches the use of unsupported catalysts of silver and thallium selenide. No prior art references are known that teach that thallium in selected amounts can be used as a promotor of silver-based ethylene oxide catalysts.

SUMMARY OF THE INVENTION

It has now been found that certain materials comprising silver deposited on a refractory support exhibit improved selectivity as catalysts for the partial oxidation of ethylene to ethylene oxide when compounds of thallium in thallium concentrations ranging from about $0.5 \times 10^{-3}$ to about $1.5 \times 10^{-3}$ gew/kg of total catalysts are deposited on the catalyst support.

DESCRIPTION OF THE PREFERRED EMBODIMENTS

The Catalyst of the Invention

When supported silver catalyst materials are prepared by the deposition of thallium on support material with surface areas ranging from about 0.03 to about 5 square meters per gram, a catalyst superior in selectivity for ethylene oxide production is produced.

Catalysts in accord with this invention comprise a porous refractory support having deposited on its exterior and interior (pore) surfaces from about 1% to about 25% by weight, based on total catalyst, of silver and certain amounts of thallium metal compounds.

The thallium of this invention is thought to be present on the catalysts in the form of its oxide and/or salts rather than as the free metal. Silver, on the other hand, is present on the finished catalysts as silver metal. The exact form of thallium on the finished catalyst is not known. However, the heat treatments given to the impregnated support will most likely convert the thallium salts to an oxygen-contianing compound as, for example, an oxide or hydroxide. The exact composition or structure of this oxygen-containing compound has not been determined, but most likely it will depend upon the thallium salts and the type of support used. By way of explanation and without intending to limit the scope of the invention, it is hypothesized that the oxygen-containing compound may somehow form a complex with the catalyst support surface rather than simply being deposited as an inert substance upon the support surface. For example, when the thallium salt is deposited upon an alumina support it is though that an aluminum-thallium metal-oxygen complex is formed. For sake of clarity in this specification and claims the amount of thallium compound present on the catalyst support has been expressed as the gram equivalent weight of the metal rather than the oxide.

The amount of thallium needed to provide enhanced selectivity depends on various factors. As the concentration of thallium in catalysts with a given silver level and given surface area is increased from zero, the selectivity of the catalyst for this production of ethylene oxide increases up to a certain point. At some thallium concentration, dependent upon support surface area and silver loading and possibly other factors, the selectivity reaches an optimum. At thallium concentrations beyond this optimum, the selectivity begins to decrease, although satisfactory catalysts within the scope of this invention may still be obtained. Preferably, thallium concentrations range from about $0.01 \times 10^{-3}$ gram atomic weight per kilogram (gaw/kg) of finished total catalyst to about $7.5 \times 10^{-3}$ gaw/kg of total catalyst, more preferably between about $0.03 \times 10^{-3}$ gaw/kg to about $5 \times 10^{-3}$ gaw/kg of total catalyst, even more preferably between about $0.2 \times 10^{-3}$ to about $3 \times 10^{-3}$ gaw/kg of the catalyst, and most preferably between about $0.5 \times 10^{-3}$ to about $1.5 \times 10^{-3}$ gaw/kg of total catalyst.

The thallium of this invention may be added at various stages in the preparation of the catalyst. It may be added to the support prior to deposition of the silver or it may be deposited simultaneously on the support with the silver, or, alternately, it may be deposited on the support after the silver has been deposited. Other promoters, such as for example, the alkali and alkaline earth metals may incidentially be present with the thallium without removing the catalyst from the scope of this invention. It is, for example, not unusual for substantial amounts, often up to about 10,000 ppm by weight of an alkali metal such as potassium, to be present within the porous support due to use of support materials containing naturally occuring alkali metals or inadvertent alkali metal addition during support manufacture.

Catalysts according to this invention preferably contain from about 1% to about 25% by weight based on the total catalyst of silver as silver metal. Preferably they contain from about 2 to about 20 percent and most preferably from about 4% to about 16% by weight of silver. The use of larger amounts of silver is not excluded but is generally economically unattractive. The silver is deposited over the interior and exterior surfaces of the catalyst support and should be evenly dispersed over these surfaces.

The exact physical form of the silver upon the support can vary and does not appear to be critical to the invention. Very excellent results are obtained with the thallium promoted catalyst of this invention, however, when the silver is present in the form of uniformly spaced, discontinuous, adherent, discrete particles having a uniform diameter of less than one micron (10,000 Å). Preferred results are obtained with this type of catalyst when the silver particles have diameters of from about 1000 to about 10,000 Å and most preferred catalysts have silver particles of an average diameter in the range of from about 1500 to about 7500 Å.

The support employed in these catalysts in its broadest aspects is selected from the large number of conventional, porous, refractory catalyst carriers or support materials which are essentially inert in the presence of the ethylene oxidation feeds, products and reaction conditions. Such conventional materials may be of natural or synthetic origin and preferably are of a macroporous structure, that is, a structure having a surface area below about 5 m$^2$/g and preferably below about 3 m$^2$/g. These support materials typically have an apparent porosity of greater than 20%. Very suitable supports comprise those of siliceous and/or aluminous composition. Specific examples of suitable supports are the aluminum oxides (including the materials sold under the trade name "Alundum"), charcoal, pumic, magnesia, zirconia, kieselguhr, fuller's earth, silicon carbide, porous agglomerates comprising silicon and/or silicon carbide, silica, magnesia, selected clays, artificial and natural zeolites and ceramics. Refractory supports particularly useful in preparation of catalysts in accordance with this invention comprise the aluminous materials, in particular those containing alpha alumina. In the case of alpha alumina containing supports, preference is given to those having a specific surface area as measured by B.E.T. method of from about 0.03 m$^2$/g to about 5 m$^2$/g and an apparent porosity as measured by conventional mercury or water absorption techniques of from about 10% to about 50% by volume. The B.E.T. method for determining specific surface area is described in detail in Brunauer, S., Emmet, P. H., and Teller, E., *J. Am. Chem. Soc.*, 60, 309–16 (1938).

When certain types of apha alumina-containing supports are employed, the advantages of thallium addition of this invention are especially emphasized. These alpha alumina supports have relatively uniform pore diameters and are more fully characterized by having (1) B.E.T. specific surface areas of from about 0.03 m$^2$/g to about 5 m$^2$/g, preferably about 0.05 m$^2$/g to about 3 m$^2$/g. The supports are preferably shaped into particles, chunks, pieces, pellets, rings, spheres, and the like of a size suitable for employment in fixed bed applications. Conventional commercial fixed bed ethylene oxidation reactors are typically in the form of a plurality of parallel elongated tubes (in a suitable shell) approximately 1 to 2 inches in diameter and 24 to 45 feet long filled with catalyst. In such reactors, it is desirable to employ a support formed into a rounded shape, such as for example, spheres, pellets, rings, tablets, and the like, having diameters of from about 0.1 inch to about 0.8 inch.

The Catalyst Preparation

The catalysts of this invention are prepared by a technique in which the thallium in the form of a salt or compound is deposited on the catalyst support prior to, simultaneous with or subsequent to the deposition of the silver.

A great variety of methods for adding silver to supports are known. In a typical method, the support may be impregnated with an aqueous solution of silver nitrate, dried and the silver reduced with hydrogen or hydrizine as described in U.S. Pat. No. 3,575,888, issued Apr. 20, 1971, to Long. In another technique the support may be impregnated with an ammoniacal solution of silver oxalate or carbonate and the silver metal formed by thermally decomposing the salt. Silver may be added as well by the technique disclosed in U.S. Pat. No. 3,702,259 of Nielsen, wherein the support is impregnated with special aqueous solutions of silver salts and combinations of ammonia, vicinal alkanolamines and vicinal alkyldiamines and then thermally treated. Other possible methods for adding silver include impregnating a support with an ethanolamine-containing solution of silver salt and then reducing, as disclosed by Japanese Pat. No. 19606/1971, or by adding a slurry of fine particles of silver carbonate to the support and thermally decomposing as described by Endler in U.S. Pat. No. 3,043,854 issued July 10, 1962. In each of these techniques, silver is added to the support when the support is contacted with a liquid phase, either a silver solution or a slurry of silver particles.

Suitable thallium salts generally include all those which are soluble in aqueous liquid phase. In this regard, to unusual effectiveness is observed with use of any particular anion in the thallium salts. For example, nitrates, nitrites, chlorides, iodides, bromates, oxalates, acetates, tartrates, lactates, isopropoxides, and similar common salts may be used. However, thallium salts should be avoided which react with the silver present in the silver liquid impregnating solution such as to cause silver salts to precipitate prematurely out of an impregnating solution. For example, thallium chloride should not be used in impregnation techniques which use an aqueous silver nitrate solution but can be used in such a technique with an aqueous solution of silver amine complexes from which silver chloride will not precipitate.

A particularly effective method of depositing the silver is where the silver is added to the support from a basic solution, particularly from a nitrogenous base-containing basic solution. Examples of these nitrogenous bases are ammonia, the alkylamines and the alkanolamines.

In a particularly preferred modification, the silver addition to the catalyst support is made by techniques such as those disclosed in U.S. Pat. No. 3,702,259 issued Nov. 7, 1972, to Nielsen. This preferred preparation method involves impregnation of an alumina support with certain aqueous silver salt solutions and a subsequent thermal reduction of the silver salt. The silver impregnation solution consists essentially of:

A. a silver salt of a carboxylic acid,

B. an organic amine alkaline solubilizing/reducing agent, and

C. and additional aqueous solvent as is required to achieve the desired silver level Suitable carboxylic acid silver salts include carbonate and the silver salts of mono-and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution used in this preparation method. Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are preferred. They are the following:

A. vicinal alkylenediamines of from 2 to 4 carbon atoms;

B. mixtures of (1) vicinal alkanolamines of from 2 to 4 carbon atoms and (2) vicinal alkylenediamines of from 2 to 4 carbon atoms;

C. mixtures of vicinal alkylenediamines of from 2 to 4 carbon atoms and ammonia; and D. mixtures of vicinal alkanolamines of from 2 to 4 carbon atoms and ammonia. These preferred solubilizing/reducing agents are generally added in the amount of from 0.1 to 10 moles per mole of silver present.

Very preferred as solubilizing/reducing agents are:

A. ethylenediamine,

B. ethylenediamine in combination with ethanolamine,

C. ethylenediamine in combination with ammonia and

D. ethanolamine in combination with ammonia.

Ethylenediamine, alone or in combination with ethanolamine, is most preferred.

When ethylenediamine is used as the sole solubilizing/reducing agent, it is necessary to add amounts of the amine in the range of from 0.1 to 5.0 moles of ethylenediamine per mole of silver.

When ethylenediamine and ethanolamine together are used as solubilizing/reducing agent, it is suitable to employ from 0.1 to 3.0 moles of ethylenediamine per mole of silver and from 0.1 to 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

In one particular embodiment of this invention wherein the thallium is deposited prior to the silver, catalysts are prepared by (A) contacting a suitable solid porous refractory support with a liquid phase which contains a suitable amount of dissolved thallium salts, or compounds (B) at least partially drying this impregnated support sufficiently to allow the impregnation of step (C) and (C) recontacting the thallium impregnated support with a liquid phase which contains an amount of silver, either as silver compounds dissolved in the liquid phase or as a slurry of silver particles in an amount sufficient to deposit from 1 to 25% by weight of silver on the support surface and (D) thermally treating the resulting product as is necessary in the presence of a reducing agent to convert the silver compound to silver metal. The exact concentrations of thallium salts and silver compounds employed in the impregnating solution may generally require some routine experimentation since the amount of thallium salts and silver compounds deposited will depend in part upon the porosity of the catalyst support. However, methods of varying the amount of thallium and silver deposited are conventional, as is the analytical determination of the amount of these materials actually present.

Preferably the impregnating liquid in step A above contains the thallium salt in such concentration as to produce in the final product a thallium metal concentration from about 0.01 to about 7.5 and more preferably from about 0.03 to about 5 even more preferably from about 0.2 to about 3 and most preferably from about 0.5 to about 1.5 milligram atomic weights per kilogram total catalyst.

Also within the scope of the invention is an alternative method of depositing the thallium salt on the support surface which provides a ready means of controlling the amount of thallium deposited within the ranges preferred in this invention. This method involves deposition of larger than required amounts of the thallium salts according to step (A) in the general procedure described above followed by contacting the catalyst particles so obtained after either step (B) or step (D) of the procedure described above with a suitable solvent, for example an anhydrous alkanol of 1 or 2 carbon atoms, methyl or ethyl acetate, tetrahydrofuran, etc. The thallium compounds contemplated by this invention are soluble in the solvents described to a sufficient degree that one or more washings with these solvents will selectively remove the excess thallium such that the amount remaining intact on the support surface falls within the desired concentration range. This method then provides a ready means of adjusting the thallium concentration from levels in excess of those preferred, whether the result of purposeful or inadvertent actions, to specific concentrations desired, by a process which is readily applicable to large plant scale operations.

An excellent method for adding the desired thallium is to dissolve it as suitable salts or compounds in an aqueous phase in an amount regulated to give the desired thallium addition to the finished catalyst when the support is contacted therewith. Suitable thallium salts generally include all those which are soluble in an aqueous phase. In this regard, no unusual effectiveness is observed with use of any particular anion in the thallium salts. For example, hydroxide, nitrates, chlorides, iodides, bromates, oxalates, acetates tartrates, lactates, isopropoxides, and similar common thallium salts may be used. The support after impregnation with the thallium salt is dried in any suitable manner. For example, by increasing the temperature to a value between about 100° C. to 200° C. for a time from about 0.1 to about 8 hours with multiple temperatures being suitable and conducting an inert gas over the heated support. Suitable inert gases are nitrogen, air, hydrogen, noble gases, carbon dioxide, methane and mixtures of these gases. Drying can be performed at atmospheric, sub-, and super atmospheric pressures. Vacuum and freeze-drying are also suitably employed. Thus, in a particularly preferred embodiment wherein the thallium is deposited prior to the silver, catalysts of this invention are prepared by (A) impregnating a porous aluminous support with an aqueous solution of thallium salt, (B) drying the impregnated support in a stream of nitrogen at about 100° C. to about 200° C. for about 0.1 to 4 hours sufficiently to allow the impregnation of step (C), (C) contacting the dried, impregnated support with a solution of silver salts, preferably a solution prepared by utilizing nitrogenous bases as described above in the method of Nielsen, and (D) maintaining the product of (C) at a temperature of from about 100° C. to about 500° C., optionally in the presence of a reducing agent, for a period of time sufficient to convert the silver salt to silver metal.

As already noted, it is frequently desirable that only certain controlled, optimum amounts of thallium of the invention be present, these optimum amounts being a function of the surface area of the catalyst support and of the silver loading. These amounts are achieved by either controlled addition of thallium to the support in the first impregnation step or by controlled removal of excess thallium from the impregnated catalyst support either before or after the silver impregnation step.

Subsequent to the use of any of these methods, the impregnated support is then heated in a non-oxidizing atmosphere at a temperature of from 100° to 375°, preferably from 125° to 325° C., for the time, typically 0.1 to 8 hours, required to decompose the silver salt and form the adherent particulate deposit of metallic silver on the surfaces. Lower temperatures do not adequately decompose the silver salt and should be avoided. More then one temperature may be employed.

In another particular embodiment of this invention wherein the thallium is deposited simultaneously with the silver, catalysts are prepared by (A) contacting a suitable solid porous refractory support with a liquid phase which contains an amount of silver, either as silver compounds dissolved in the liquid phase or as a slurry of silver compound particles, in an amount sufficient to deposit from 1 to 25% by weight of silver on the support surface and a desired amount of dissolved salts or compounds of thallium, thereby coincidentally depositing these silver compounds and thallium salts upon the catalyst surface; and (B) thermally treating the resulting silver compound- and thallium salt-containing product in the presence of a reducing agent to convert the silver compound to silver metal. Suitable impregnating solutions contain, for example, from about 3 to about 40% by weight of silver salts and from about 25 to about 1000 ppm by weight of thallium, although other concentrations are useful. The exact concentrations employed generally may require some routine experimentation since the amount of thallium deposited from a solution, will depend in part on the porosity of the catalyst support. However, methods of varying the amount of silver and/or thallium deposited are conventional, as is the analytical determination of the amount of the materials actually deposited.

Also within the scope of the invention is an alternative method of coincidentally depositing the silver and thallium salt on the support surface, which provides a ready means of controlling the amount of thallium deposited. This method involves deposition of larger than the desired amounts of the thallium coincidentally with the silver according to the general procedure described above followed by contacting the catalyst particles so prepared with an anhydrous alkanol of 1 to 2 carbon atoms. The thallium salts contemplated by this invention are soluble in the alkanol solvents described to a sufficient degree that one or more washings with the alkanol solvents will selectively remove the excess coincidentally deposited thallium such that the amount remaining intact on the support surface falls within the concentration range desired. This method then provides a ready means of adjusting the thallium concentration from levels in excess of those preferred, whether the result of purposeful or inadvertent actions, to specific, desired concentrations by a process which is readily applicable to large plant scale operations.

The thallium addition of this invention is especially effective when used in conjunction with silver catalyst preparation techniques wherein silver is added to the support from a basic solution, particularly from a nitrogenous base-containing basic solution, as for example, the techniques of Nielsen described above.

Thus, in a particularly preferred embodiment, catalysts of this invention are prepared by (A) adding to a porous aluminous support from about 1% by weight to about 25% by weight of silver in the form of water-soluble silver salts and desired amounts of thallium in the form of water-soluble salts by contacting the support with an alkaline aqueous solution of the silver and thallium salts; and (B) maintaining the product of step (A) at a temperature of from about 100° C. to about 500° C. in the presence of a reducing agent for a period sufficient to convert the silver salts to silver metal.

As already noted, it is frequently desirable that only certain controlled optimum amounts of the thallium of this invention be present. These amounts are achieved by either controlled addition of thallium to a thallium-free silver solution, by controlled removal of thallium from a thallium-rich solution or by controlled removal of thallium from the support surface after deposition of larger than desired amounts of thallium by use of suitable solvents such as those described above, e.g. alkanols of 1 or 2 carbon atoms, etc.

Subsequent to the use of any of these methods, the impregnated support is then heated to a non-oxidizing atmosphere at a temperature of from 100° to 375°, preferably from 125° to 325° C., for the time, typically ½ to 8 hours, required to decompose the silver salt and form the adherent particulate deposit of metallic silver on the surfaces. Lower temperatures do not adequately decompose the silver salt and should be avoided. More than one temperature may be employed.

In another particular embodiment wherein the thallium is deposited subsequent to the deposition of the silver, the catalysts of this invention are prepared by (A) contacting a suitable solid porous refractory support with a liquid phase which contains an amount of silver, either as silver compounds dissolved in the liquid phase or as a slurry of silver particles in an amount sufficient to deposit from 1% to 25% by weight of silver on the support surface, (B) thermally treating the resulting product as is necessary in the presence of a reducing agent to convert the silver compound to silver metal, (C) recontacting the silver metal impregnated support with a liquid phase which contains a suitable amount of thallium salts or compounds and (D) drying the resulting product. The exact concentration of silver compounds and thallium salts employed in the impregnation solutions may generally require some routine experimentation since the amount of silver compounds and thallium salts deposited will depend in part upon the porosity of the catalyst support. However, methods of varying the amount of silver and thallium deposited are conventional, as is the analytical determination of the amount of the materials actually present.

Preferably the impregnating liquid in step C above contains the thallium salt in such concentration as to produce in the final product a thallium metal concentration from about 0.01 to about 7.5 and more preferably from about 0.03 to about 5 and even more preferably from about 0.2 to about 3 and most preferably from about 0.5 to about 1.5 milligram weights per kilogram total catalyst.

Also within the scope of the invention is an alternative method of depositing the thallium salt on the support surface area which provides a ready means of controlling the amount of thallium deposited within the ranges preferred in this invention. This method involves deposition of larger than desired amounts of thallium salts according to step (C) in the general procedure described above followed by contacting the catalyst particles so obtained after step (D) with a suitable solvent, for example, an anhydrous alkanol of 1 or 2 carbon atoms, methyl or ethyl acetate, tetrahydrofuran, etc. The thallium salts contemplated by this invention are soluble in the solvents described to a sufficient degree that one or more washings with these solvents will selectively remove the excess thallium such that the amount remaining intact on the support surface falls within the desired concentration range. This method then provides a ready means of adjusting the thallium concentration from levels in excess of those preferred whether the result of purposeful or inadvertent actions, to specific concentrations, by a process which is readily applicable to large plant scale operations.

An excellent method for adding the desired thallium is to dissolve it as suitable salts in an aqueous phase in an amount regulated to give the desired thallium addition to the finished catalyst when the support is contacted therewith. Suitable thallium salts generally include all those which are soluble in an aqueous phase. In this regard, no unusual effectiveness is observed with use of any particular anion in the alkali metal salts. For example, hydroxides, nitrates, chlorides, iodides, bromates, oxalates, acetates, tartrates, lactates, isopropoxides, and similar common thallium salts may be used. The support after impregnation with the thallium salts is dried in any suitable manner. For example, by increasing the temperature to a value between about 100° C. to 200° C. for a time from about 0.1 to about 8 hours with multiple temperatures being suitable and conducting an inert gas over the heated support. Suitable inert gases are nitrogen, air, hydrogen, noble gases, carbon dioxide, methane and mixtures of these gases. Drying can be performed at atmospheric, sub-, and super atmospheric pressures. Vacuum and freeze-drying are also suitably employed.

Thus, in a particularly preferred embodiment wherein the thallium is deposited subsequent to the silver, catalyst of this invention are prepared by (A) contacting a porous aluminous support with a solution of silver salts, preferably a solution prepared by utilizing nitrogenous bases as described above in the method of Nielsen, (B) thermally treating the resulting product at a temperature of preferably from about 100° C. to about 375° C., more preferably from about 125° C. to about 325√ C. for from about 0.1 hours to about 8 hours in order to decompose the silver salt and form the adherent particulate deposit of metallic silver on the surfaces of the support (C) recontacting the silver metal impregnated support with an aqueous solution which contains a suitable amount of water soluble thallium salts and (D) drying the impregnated support in a stream of nitrogen at about 100° C. to about 200° C. for from about 0.1 hours to about 4 hours.

As already noted, it is frequently desirable that only certain controlled, optimum amounts of thallium of the invention be present, these amounts being a function of the surface area of the catalyst support and of the silver loading. These amounts are achieved by either controlled addition of thallium to the support in the impregnation step or by controlled removal of excess thallium from the catalyst product.

Ethylene Oxide Production

The thallium-promoted silver catalysts have been shown to be particularly selective catalysts in the direct controlled oxidation of ethylene with molecular oxygen to ethylene oxide. The conditions for carrying out such an oxidation reaction in the presence of the silver catalysts of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Pressures in the range of from about atmospheric to about 500 psi are generally employed. Higher pressures may, however, be employed. The suitable oxygen charge may consist essentially of relatively pure oxygen, a concentrated oxygen stream comprising oxygen in major amounts with lesser amounts of one or more diluents such as nitrogen, argon, etc., or another oxygen-containing stream such as air. The use of the present novel silver catalysts in ethylene oxidation reactions is in no way limited to the use of specific conditions among those which are known to be effective.

In a preferred application of the silver catalysts of the invention ethylene oxide is produced when an oxygen-containing gas of not less than 95% oxygen is contacted with ethylene in the presence of the present catalysts at a temperature in the range of from 210° C. to 285° C. and preferably 225° C. to 270° C.

The resulting ethylene oxide is separated and recovered from the reaction products by conventional methods known and used in the art. Use of the silver catalysts of the invention in ethylene oxide production processes gives higher overall ethylene oxidation selectivities to ethylene oxide at a given ethylene conversion than is possible with conventional silver catalysts.

While the reason for these higher selectivities observed with catalysts of this invention is not fully understood, experiments have indicated that conventional silver catalyts (not containing thallium) cause ethylene oxide to combust after formation while silver catalysts containing thallium according to this invention do not cause as extensive ethylene oxide combustion.

Preparation of catalysts according to the invention and their use in the production of ethylene oxide will be further described by the following examples which are provided for illustration and are not to be construed as limiting the invention.

ILLUSTRATIVE EMBODIMENT

Part A.

Thallium-containing catalysts were prepared in accordance with this invention utilizing as a support 3/16-inch diameter rings of alpha-alumina. This support contained 99.3% by weight alpha-alumina, 0.4% silica, and 0.3% of other metal oxides and had a surface area of 0.24 m²/g and an apparent porosity of 48–49% by volume. This support had a median pore diameter of 4.4 microns as determined by mercury porosimetry. Eighty percent of its pores had diameters in the range of from 1.5 to 15 microns.

Several catalysts were prepared by impregnating the above described support with aqueous solutions of silver salt containing differing amounts of thallium. Reagent grade silver oxide was mixed with an aqueous solution of reagent grade oxalic acid dissolved in ethylenediamine to form an about 2 molar solution of $Ag_2(EN)_2C_2O_4$. Ten percent by volume of ethanolamine (about 0.4 moles of ethanolamine per mole of silver) was then added to complete the solubilizing/reducing agent combination. This solution contained about 22% by weight of silver. Thallium acetate, to achieve about 280–800 ppm by weight of thallium, was added to the various solutions. The catalyst support was impregnated with these thallium-containing silver solutions and vacuum was applied to ensure complete saturation. Excess liquid was drained off and the support was immediately placed in a forced air oven at 290° C. to dry the catalyst and reduce the silver salt to silver metal. Total heating time was about 3 hours. The silver and thallium contents of the catalysts (A–F) were determined and are given in Table I.

Part B.

For purpose of comparison the preparation of Part A was repeated with the difference that no thallium salt was added to the impregnation solution. This catalyst is also listed in Table I as Catalyst G. A catalyst (H) containing only thallium was also prepared.

Part C.

The thallium-modified catalysts, the thallium-free catalyst and the silver-free catalysts were comparatively tested as catalysts for the production of ethylene oxide. In a representative experiment, 5/16-inch rings of catalyst were crushed and 3.5 grams of 30/40 mesh particles of crushed catalyst were charged to a 0.20-inch diameter by 5-inch long reaction bed. A mixture of air and ethylene was passed over the catalyst in the presence of a chlorine-containing moderator at the following reaction conditions:

| | |
|---|---|
| Pressure, psig | 200 |
| Space Velocity, hours$^{-1}$ | 3300 |
| Ethylene in charge, % m | 30 |
| Ethylene/O₂ ratio | 3.75 |
| Moderator Concentration, ppm of equivalent Chlorine | 10–15 |

The reaction temperature was adjusted to provide an oxygen conversion of 52% and the selectivity to ethylene oxide was determined. The results of these experiments are shown in Table I.

TABLE I

ETHYLENE OXIDE CATALYST

| Catalyst | Silver content | Thallium Content Gram atom wt. per kg of total catalyst | Reactor Temp. to achieve 52% O₂ Conversion, °C. | Oxidation Selectivity to Ethylene Oxide, % |
|---|---|---|---|---|
| A | 8.0 | $2.5 \times 10^{-4}$ | 244.0 | 74.0 |
| B | 7.8 | $4.9 \times 10^{-4}$ | 267.0 | 74.6 |
| C | 7.8 | $7.4 \times 10^{-4}$ | 247.0 | 77.6 |
| D | 7.8 | $9.8 \times 10^{-4}$ | 255.5 | 78.0 |
| E | 7.8 | $13.7 \times 10^{-4}$ | 260.0 | 76.5 |
| F | 8.0 | $20.0 \times 10^{-4}$ | (257.0)* | (60.0)* |
| G | 7.8 | - 0 - | 251.0 | 69.5 |
| H | 0 | $7.8 \times 10^{-4}$ | No conversion | None detected |

*24% O₂ Conversion

We claim as our invention:

1. A catalyst for the production of ethylene oxide by the controlled incomplete oxidation of ethylene with molecular oxygen which comprises a porous refractory support having deposited on its exterior and interior pore surfaces metallic silver and compounds of thallium wherein the silver ranges from about 1 percent to about 25 percent by weight and the thallium concentration ranges from about $0.5 \times 10^{-3}$ to about $1.5 \times 10^{-3}$ gram atomic weight per kilogram (gaw/kg) of total catalyst.

2. The catalyst of claim 1 wherein the silver ranges from about 2 to about 20 percent by weight.

3. The catalyst of claim 2 wherein the silver ranges from about 4 to about 16 percent by weight.

4. The catalyst of claim 1 wherein the surface area of the support ranges from about 0.03 to about 5 square meters per gram (m²/g).

5. The catalyst of claim 4 wherein the surface area of the support ranges from about 0.05 to about 3 m²/g.

6. The catalyst of claim 1 wherein the support comprises alpha alumina.

7. The catalyst of claim 1 wherein the support comprises siliceous material.

8. A catalyst for the production of ethylene oxide by the controlled incomplete oxidation of ethylene with molecular oxygen consisting essentially of a porous alpha alumina support having a surface area of from about 0.03 m²/g to about 5 m²/g and having deposited on its exterior and pore surfaces from about 1 to about 25 percent by weight of silver and from about $0.5 \times 10^{-3}$ to about $1.5 \times 10^{-3}$ gaw/kg of total catalyst of thallium.

9. The catalyst of claim 8 wherein the silver ranges from about 2 to about 20 percent by weight.

10. The catalyst of claim 8 wherein the surface area of the support ranges from about 0.05 to about 3 m²/g.

11. A process for preparing a catalyst for the production of ethylene oxide by the controlled incomplete oxidation of ethylene with molecular oxygen which comprises:
   (a) contacting a porous refractory support having a surface area from about 0.03 to about 5 m²/g with a liquid phase having dissolved therein a thallium salt- or mixtures of thallium salts in an amount sufficient to deposit from about $0.5 \times 10^{-3}$ to about $1.5 \times 10^{-3}$ gaw/kg of total catalyst of thallium,
   (b) at least partially drying this impregnated support sufficiently to allow the impregnation of step (c),
   (c) recontacting the thallium impregnated support with a liquid phase containing dissolved therein a silver compound in an amount sufficient to deposit from about 1 to about 25 percent by weight of silver on the support surface, and, (d) thermally treating the resulting product in the presence of a reducing agent in order to convert the silver compound to silver.

12. The process of claim 11 wherein the silver deposited ranges from about 2 to about 20 percent by weight.

13. The process of claim 12 wherein the silver deposited ranges from about 4 to about 16 percent by weight.

14. The process of claim 11 wherein the surface area of the support ranges from about 0.5 to about 3 m$^2$/g.

15. The process of claim 11 wherein the support comprises alpha alumina.

16. A catalyst prepared by the process of claim 11.

17. A process for preparing a catalyst for the production of ethylene oxide by the controlled incomplete oxidation of ethylene with molecular oxygen which comprises:

(a) contacting a porous refractory support having a surface area from about 0.03 to about 5 m$^2$/g with a liquid phase having dissolved therein a silver compound sufficient to deposit on the support from about 1 to about 25 percent by weight of silver and thallium salt or salts sufficient to deposit on the support from about $0.5 \times 10^{-3}$ to about $1.5 \times 10^{-3}$ gaw/kg of total catalyst of thallium thereby depositing silver compounds and thallium salts on the support, and, (b) thermally treating the resulting product in the presence of a reducing agent to convert the silver compound to silver metal.

18. The process of claim 17 wherein the silver deposited ranges from about 2 to about 20 percent by weight.

19. The process of claim 18 wherein the silver deposited ranges from about 4 to about 16 percent by weight.

20. The process of claim 17 wherein the surface area of the support ranges from about 0.05 to about 3 m$^2$/g.

21. The process of claim 17 wherein the support comprises alpha alumina.

22. A catalyst prepared by the process of claim 17.

23. A process for preparing a catalyst for the production of ethylene oxide by the controlled incomplete oxidation of ethylene with molecular oxygen which comprises:

(a) contacting a porous refractory support having a surface area from about 0.03 to about 5 m$^2$/g with a liquid phase have dissolved therein a silver compound sufficient to deposit on the support from about 1 to about 25 percent by weight of silver, (b) thermally treating the resulting product in the presence of a reducing agent in order to convert the silver compound to silver, (c) recontacting the silver-metal impregnated support with a liquid phase having dissolved therein a thallium salt or mixtures of thallium salts sufficient to deposit on the support from about $0.5 \times 10^{-3}$ to about $1.5 \times 10^{-3}$ gaw/kg of total catalyst of thallium, (d) drying the resulting catalyst to produce the finished catalyst.

24. The process of claim 23 wherein the silver deposited ranges from about 2 to about 20 percent by weight.

25. The process of claim 24 wherein the silver deposited ranges from about 4 to about 16 percent by weight.

26. The process of claim 23 wherein the surface area of the support ranges from about 0.05 to about 3 m$^2$/g.

27. The process of claim 23 wherein the support comprises alpha aluminum.

28. A catalyst article prepared by the process of claim 23.

* * * * *